(12) United States Patent
Sournac et al.

(10) Patent No.: US 10,806,597 B2
(45) Date of Patent: Oct. 20, 2020

(54) METHOD FOR MAKING AN IMPLANT, NOTABLY A VERTEBRAL OR INTERVERTEBRAL IMPLANT, AND IMPLANT OBTAINED BY THIS METHOD

(71) Applicant: MEDICREA INTERNATIONAL, Rillieux la Pape (FR)

(72) Inventors: Denys Sournac, Reyrieux (FR); Thomas Mosnier, Rochetaillee sur Saone (FR); David Ryan, Collonges au Mont d'Or (FR)

(73) Assignee: MEDICREA INternational, Rillieux la Pape (FR)

( * ) Notice: Subject to any disclaimer, the term of this patent is extended or adjusted under 35 U.S.C. 154(b) by 206 days.

(21) Appl. No.: 16/086,968

(22) PCT Filed: Mar. 27, 2017

(86) PCT No.: PCT/IB2017/051733
§ 371 (c)(1),
(2) Date: Sep. 20, 2018

(87) PCT Pub. No.: WO2017/168304
PCT Pub. Date: Oct. 5, 2017

(65) Prior Publication Data
US 2019/0105172 A1 Apr. 11, 2019

(30) Foreign Application Priority Data
Mar. 30, 2016 (FR) ........................... 16 52714

(51) Int. Cl.
*A61F 2/44* (2006.01)
*A61F 2/46* (2006.01)
(Continued)

(52) U.S. Cl.
CPC .......... *A61F 2/447* (2013.01); *A61B 17/7035* (2013.01); *A61F 2/4611* (2013.01);
(Continued)

(58) Field of Classification Search
CPC ................................. A61F 2/447; A61F 2/446
See application file for complete search history.

(56) References Cited

U.S. PATENT DOCUMENTS

| 5,360,450 | A  | * | 11/1994 | Giannini | ................. | A61L 27/18 |
|           |    |   |         |          |                   | 623/21.19  |
| 6,723,128 | B2 | * | 4/2004  | Uk       | ......................... | A61F 2/446 |
|           |    |   |         |          |                   | 623/17.15  |

(Continued)

FOREIGN PATENT DOCUMENTS

| DE | 102005004563 | 8/2006 |
| DE | 102005033608 | 1/2007 |

(Continued)

*Primary Examiner* — Andrew Yang
(74) *Attorney, Agent, or Firm* — Defillo & Associates, Inc.; Evelyn A Defillo

(57) ABSTRACT

The implant (1) includes at least two assembled components, at least a first component (3) is intended to be movable relative to at least a second component (2). The method includes the steps of: designing the implant (1) such that the second component (2) at least partially envelops the first component (3) and that at least one connecting bridge (4) connects the first component to the second component, each bridge (4) having a section such that it is frangible; making the implant (1) using a so-called "3D printing" method, includes depositing on a platen, a layer of powdered fusible material, causing the particles of this layer of powder to fuse in locations corresponding to the shape which, at this layer, the first component (3, 23, 33, 53, 63) and/or the second component (2, 22, 32, 52, 62) and/or the at least one bridge (4, 24, 54, 64) have, depending on whether the first component, the second component and/or said bridge are present (Continued)

at the section the implant to be formed has at the layer; repeating these operations until the implant (1, 21, 31, 51, 61) is fully constructed, and eliminating the powder particles that are not fused.

6 Claims, 4 Drawing Sheets

(51) Int. Cl.
    *A61B 17/70*     (2006.01)
    *A61F 2/30*     (2006.01)
    *A61B 90/00*     (2016.01)

(52) U.S. Cl.
    CPC . *A61B 2090/037* (2016.02); *A61F 2002/3011* (2013.01); *A61F 2002/3054* (2013.01); *A61F 2002/30266* (2013.01); *A61F 2002/30538* (2013.01); *A61F 2002/30579* (2013.01); *A61F 2002/30593* (2013.01); *A61F 2002/30594* (2013.01); *A61F 2002/30892* (2013.01); *A61F 2002/30985* (2013.01); *A61F 2002/4629* (2013.01)

(56) References Cited

U.S. PATENT DOCUMENTS

| | | | |
|---|---|---|---|
| 6,955,691 B2 * | 10/2005 | Chae | A61F 2/446 |
| | | | 623/17.16 |
| 7,655,046 B2 * | 2/2010 | Dryer | A61F 2/4611 |
| | | | 623/17.15 |

FOREIGN PATENT DOCUMENTS

| DE | 202015001700 | 8/2015 |
|---|---|---|
| EP | 2459126 | 6/2012 |
| WO | WO 9855038 | 12/1998 |

\* cited by examiner

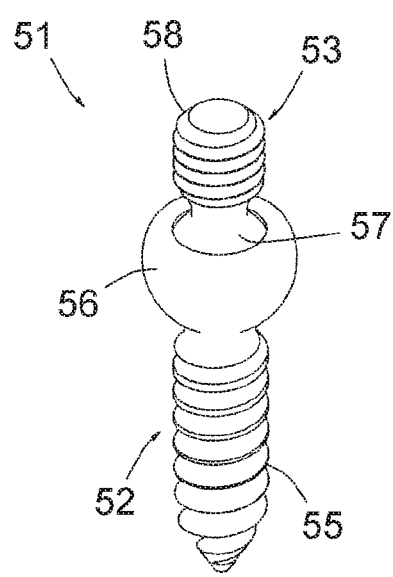
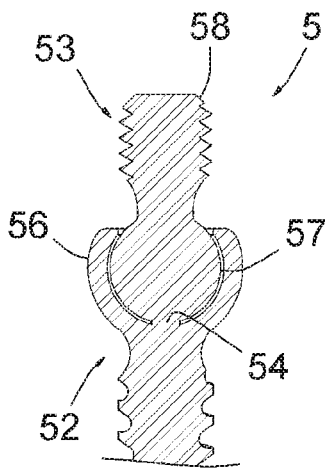
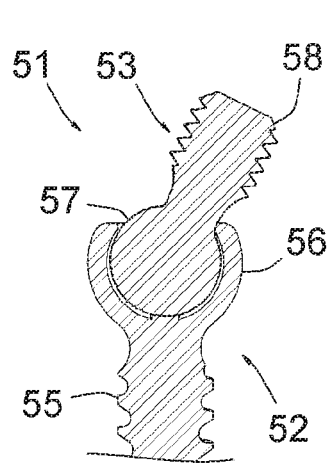
FIG. 12    FIG. 13    FIG. 14
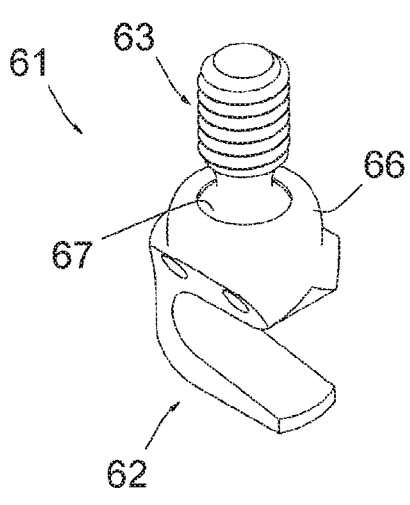
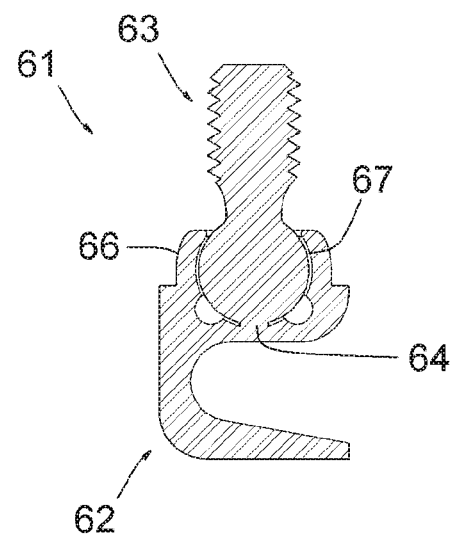
FIG. 15    FIG. 16

METHOD FOR MAKING AN IMPLANT, NOTABLY A VERTEBRAL OR INTERVERTEBRAL IMPLANT, AND IMPLANT OBTAINED BY THIS METHOD

CROSS REFERENCE TO RELATED APPLICATION

This application is a national stage entry of PCT/IB2017/051733 filed Mar. 27, 2017, under the International Convention claiming priority over French Patent Application No. 16 52714 filed Mar. 30, 2016.

FIELD OF THE INVENTION

The present invention relates to a method for manufacturing an implant, in particular vertebral or intervertebral, and the implant obtained using said method.

BACKGROUND OF THE INVENTION

It is well known to immobilize two vertebrae relative to one another using an intervertebral implant made from a rigid material, forming a cage that delimits a housing, this housing being intended to receive one or several bone grafts and/or spongy bone chips. Some intervertebral cages are implanted through a posterior approach and are called "PLIF" (acronym for Posterior Lumbar Interbody Fusion), others through an anterior approach ("ALIF", Anterior Lumbar Interbody Fusion), and still others through a transforaminal approach ("TLIF", Transforaminal Lumbar Interbody Fusion).

To provide the anchoring of PLIF or ALIF cages, it is known to provide elements deployable from the inside of the cage, in the form of prongs or anchoring tips; it is also known to provide a cage having an anterior part (i.e., the part of the cage located on the anterior side of the vertebra after implantation), the height of which is able to be increased after implantation, so as to make it possible, using this cage, to give the lumbar vertebrae back their mutual separation and their anatomical lordosis. Such a cage comprises a base structure with two branches and a wedge-forming component, movable between these branches, this wedge-forming component making it possible, through its movement relative to said branches after implantation of the cage, to deploy the anterior part of the cage.

The existing cages are made from metal, generally titanium or stainless steel; they have a relatively complex structure, and are also complex and expensive to manufacture.

A TLIF cage, as for example described in patent application publication no. EP 2,459,126 in the applicant's name, must in turn be connected to an instrument allowing it to be inserted into an intervertebral space, while being held in the extension of this instrument when it is inserted into said intervertebral space, once inserted into this space, while being able to be pivoted relative to the instrument in order to be placed in the anterior zone of the intervertebral space, and must lastly be separated from the instrument.

The connecting zone of such a cage with the instrument is generally complex and relatively expensive to manufacture. Furthermore, the existing cages and instruments do not preclude any risk of defective positioning of the cage.

It is also well known to place, on vertebrae, anchoring members to vertebrae, in particular pedicle screws or laminar hooks, allowing rigid bars for immobilizing vertebrae to be mounted on said vertebrae. Such an anchoring member is frequently "polyaxial", i.e., it comprises a distal bone anchoring part and a proximal connecting part to a bar, articulated relative to said base part. Said proximal connecting part can be in the form of a component receiving a bar (such a proximal part is called "tulip" in reference to its outer shape), or can be in the form of an articulated pin, as in particular described by patent application publication no. WO 98/55038, also in the applicant's name.

Such anchoring members are also relatively complex and expensive to manufacture.

Patent application publications no. DE 10 2005 033608 A1 and no. DE 10 2005 004563 A1 describe methods for manufacturing an implant comprising at least two components, at least a first component of which is intended to be movable relative to at least a second component, these methods including the step consisting of designing the implant such that said second component at least partially envelops said first component.

OBJECT OF THE INVENTION

The present invention aims to resolve all of the aforementioned drawbacks.

SUMMARY OF THE INVENTION

According to the invention, the method includes the following steps:

designing the implant such that at least one connecting bridge connects the first component to said second component, each bridge having a section such that it is frangible;

making the implant using a so-called "3D printing" method, consisting of:

depositing, on a platen, a layer of powdered fusible material, causing the particles of this layer of powder to fuse in locations corresponding to the shape which, at this layer, said first component and/or said second component and/or said at least one bridge have, depending on whether said first component, said second component and/or said bridge are present at the section the implant to be formed has at said layer;

repeating these operations until the implant is fully constructed, and eliminating the powder particles that are not fused.

Said first component of the implant is thus produced at the same time as said second component of the implant, with said second component at least partially enveloping said first component, as well as at least one frangible bridge connecting said first component to said second component, and the at least partial enveloping of said first component by said second component produces an assembly of said first component to said second component when each bridge is broken.

The method according to the invention thus makes it possible to produce an implant relatively simply and quickly, without subsequent assembly operations.

The frangibility of each bridge may be obtained by giving each bridge a reduced cross-section, for example smaller than 1 mm².

This frangibility may be produced in the plant, such that any debris that it may generate is eliminated during the manufacturing stage. It is, however, conceivable that the breaking of each bridge may occur during the surgical procedure, through a manual action or using an instrument.

The invention also relates to the implant obtained directly by this method.

The implant may in particular be an intervertebral cage having an anterior part, the height of which is able to be increased after implantation; said second component is then made up of a cage body forming two branches, which is deformable in this way such that anterior end portions of these branches are movable relative to one another between a close together position and a separated position; said first component is then made up of a separating wedge engaged between said branches, connected to the cage body by said at least one bridge.

The implant may also be an intervertebral cage of the "TLIF" type; said first component may then be made up of a component of revolution and said second component may be made up of a cage body forming a bearing for receiving and retaining this component of revolution; the component of revolution includes a means for connecting to an instrument for inserting/positioning the implant.

Said component of revolution and said bearing allow the pivoting mobility of said second component relative to said first component, required by this type of intervertebral cage.

Said component of revolution may in particular be a cylinder and its means for connecting to said instrument may in particular be formed by a through hole forming an inner thread arranged in said component of revolution. An instrument for placing the cage then includes a rod having a threaded distal tip intended to be screwed into this through hole of said component of revolution, the arrival of this threaded distal tip against the wall of said second component defining the bearing making it possible to immobilize said second component in a determined position relative to the instrument, in particular in a position in which this second component is in the longitudinal extension of the instrument.

The implant can also be a polyaxial pedicle screw or a polyaxial laminar hook; said first component is then formed by a connection head or a threaded pin, and said second component is intended to be engaged with a vertebra to be treated.

According to one preferred embodiment of the invention, in this case, one from among said component part and said second component has an at least partially spherical portion and the other from among said first component and said second component has a corresponding at least partially spherical cavity, intended to receive said at least partially spherical portion, said bridge being arranged between said at least partially spherical portion and the wall defining said at least partially spherical cavity.

The invention will be well understood, and other features and advantages thereof will appear, in reference to the appended diagrammatic drawing, showing, as non-limiting examples, several embodiments of the implant to which it relates.

BRIEF DESCRIPTION OF THE DRAWINGS

FIG. 12 is a perspective view of the implant according to a fourth embodiment, in this case made up of a pedicle screw with an articulated proximal pin;

FIG. 13 is a longitudinal sectional view of the implant passing through the axis of the screw, said proximal pin being immobilized in an axial position;

FIG. 14 is a view of the implant similar to FIG. 13, said proximal pin being in an inclined position; and FIGS. 15 and 16 are views of the implant according to a fifth embodiment, equivalent to FIGS. 12 and 13, respectively, in the case of a laminar hook with an articulated proximal pin.

DESCRIPTION OF THE PREFERRED EMBODIMENTS

Figure 1:
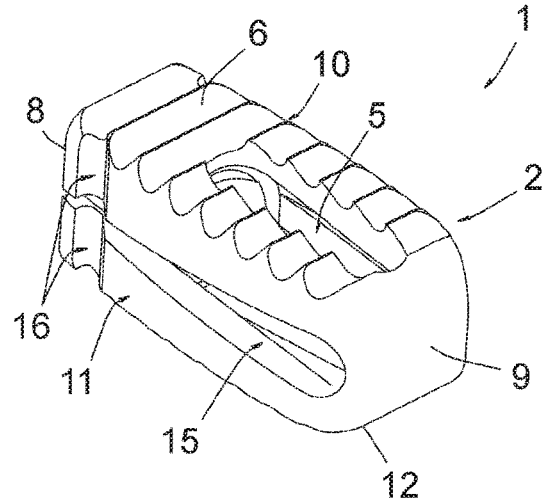
FIG. 1 is a perspective view of the implant according to a first embodiment, in this case made up of an intervertebral cage of the ALIF type, with a width suitable for a lateral placement in an intervertebral space.
Figure 2:
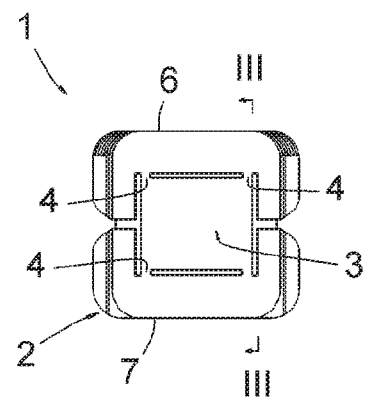
FIG. 2 is an end view thereof, from the proximal side.
Figure 3:
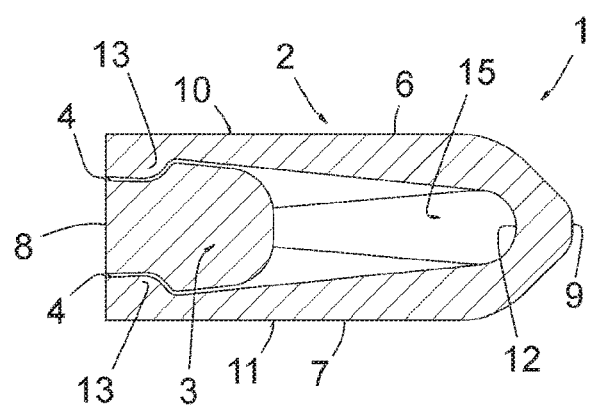
FIG. 3 is a schematic view thereof, in longitudinal cross-section.

FIGS. 1 to 3 show an intervertebral cage 1 of the ALIF type, i.e., intended to be implanted through an anterior approach.

The cage 1 is made up of a cage body 2, a separating wedge 3 and four material bridges 4 connecting this wedge 3 and the cage body 2, as shown in FIGS. 2 and 3.

The entire cage 1 is made using a so-called "3D printing" method, which consists of:

depositing, on a platen, a layer of powdered fusible material, fusing the particles of this layer of powder in determined locations, corresponding to a shape of a cross-section of the cage 1 to be produced at this layer, repeating these operations until the cage 1 is fully constructed, and eliminating the powder particles that are not fused.

Said determined locations are therefore defined, from one layer to another, by the contours, at the considered layer, of the cage body 2, the separating wedge 3 and said bridges 4, as long as said cage body 2, said separating wedge 3 and said bridges 4 are present at the section of the cage 1 to be formed at said layer.

The wedge 3 is therefore made using said method at the same time as the cage body 2, as well as the material bridges 4 connecting the wedge 3 to the cage body 2.

The cage body 2 has a cavity 5 emerging on the outside of this body by wide openings, this cavity 5 being intended to be filled with one or several spongy bone grafts or a clump of spongy bone chips.

This cage body 2 has a generally parallelepiped shape, defining a serrated upper surface 6, a lower surface 7 opposite this upper surface 6, a proximal end 8 and a distal end 9.

It will be understood that the terms "upper" and "lower" refer to the position that the cage 1 is intended to be in when it is implanted between two vertebrae, the upper surface 6 being intended to come into contact with the lower plate of the underlying vertebra while the lower surface 7 is intended to come into contact with the upper plate of the underlying vertebra. Likewise, the terms "proximal" and "distal" used in the present description should be considered, traditionally, relative to the practitioner, "proximal" describing a part of the cage 1 (or other described implants) located close to this practitioner during the placement of the implant, and "distal" therefore describing a part of the cage located further from this practitioner during the same placement.

It appears that the cage body 2 assumes the form of a horizontal U, i.e., it has an upper branch 10, a lower branch 11 across from the branch 10 and an intermediate portion 12 connecting these two branches to one another.

The two branches 10, 11 form anterior ribs 13 and are separated by a longitudinal slit 15 extending from the proximal end 8 toward a distal end 9, this slit 15 being interrupted, on the side of this distal end 9, at a curved inner wall formed by said intermediate portion 12. The slit 15 extends in a plane parallel to that along which the branches 10 and 11 extend parallel to one another and emerges in the side surfaces of the cage 1, i.e., in the surfaces thereof that are perpendicular to the upper 6 and lower 7 surfaces. In the illustrated example embodiment, the slit 15 has a thickness, i.e., a dimension perpendicular to said plane, that increases from the proximal end 8 toward the distal end 9 of the cage 1.

In reference to FIG. 3, it appears that the inner surfaces of the branches 10 and 11, i.e., the surfaces across from one another, are inclined so as to converge toward one another from the proximal end 8 of the cage 1 toward the distal end 9 thereof; these surfaces form ramps along which the wedge 3 is, after breaking of the bridges 4, able to move, as will be described later, this movement allowing a separation of the two branches 10, 11 from one another.

This FIG. 3 also shows that the anterior ribs 13 are transverse to the longitudinal direction of the cage 1 and that they make it possible to partially close, at the anterior level of this cage, the space inwardly defined by the cage body 2.

The wedge 3 has a square cross-section and forms, on the posterior side of this wedge 3, upper and lower surfaces coming into the immediate vicinity of the inner surfaces of the branches 10 and 11. These upper and lower surfaces are able to bear against these inner surfaces during the movement of the wedge 3, to perform the anterior separation of the branches 10 and 11. On the anterior side, the wedge 3 has reinforced portions having a contour that follows that of the ribs 13. The latter thus form portions partially enveloping the wedge 3, providing, after breaking of the bridges 4, the retention of this wedge 3 in the space inwardly defined by the cage body 2.

FIG. 2 shows that the four bridges 4 are located near angles formed by the wedge 3, and this FIG. 2 as well as FIG. 3 show that said bridges 4 have smaller cross-sections, smaller than 1 mm² for each bridge 4, such that these bridges 4 are sized to be frangible.

The cage body 2 further outwardly has, at its side walls, anterior recessed zones 16 that allow it to be grasped and maintained using an instrument for placing the cage 1 in an intervertebral space. This instrument (not shown) is in the form of a clamp whereof the two branches form a clamping jaw for grasping the cage 1 at recessed zones 16. The instrument also comprises a longitudinally movable rod, between the jaws of said clamping jaw.

The bridges 4 can be broken in the plant, at the end of manufacturing of the cage 1, in which case said rod only moves the wedge 3; said bridges 4 could be broken once the cage 1 is placed, in which case said rod breaks the bridges 4, then moves the wedge 3.

This movement of the wedge 3 relative to the cage body 2 in the distal direction separates the proximal end portions of the branches 10 and 11, such that the cage 1 is able to restore the mutual separation and anatomical lordosis of the lumbar vertebrae between which it is implanted.

The cage 1 shown in FIGS. 1 to 3 has a limited width, suitable for placement of this cage on a lateral side of an intervertebral space; another cage 1, identical, is in this case placed on the other lateral side of said intervertebral space.

Figure 4:
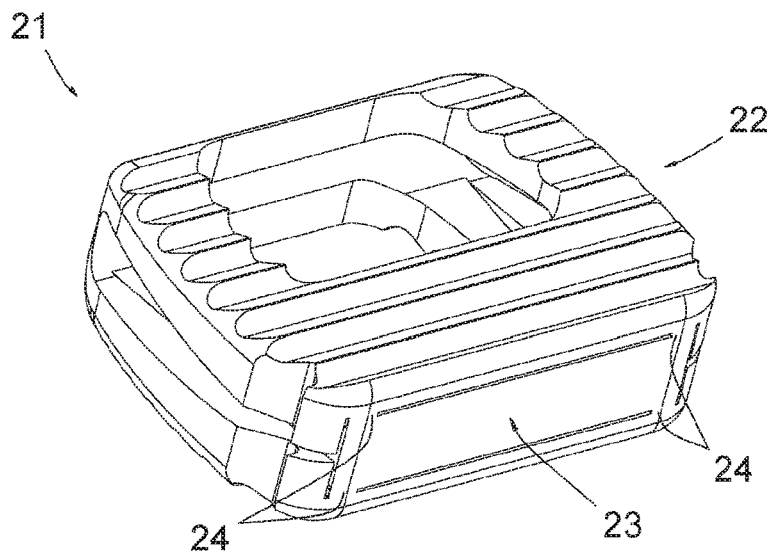
FIG. 4 is a perspective view of the implant according to a second embodiment, also made up of an intervertebral cage of the ALIF type, with a width suitable for a central placement in an intervertebral space.
Figure 5:
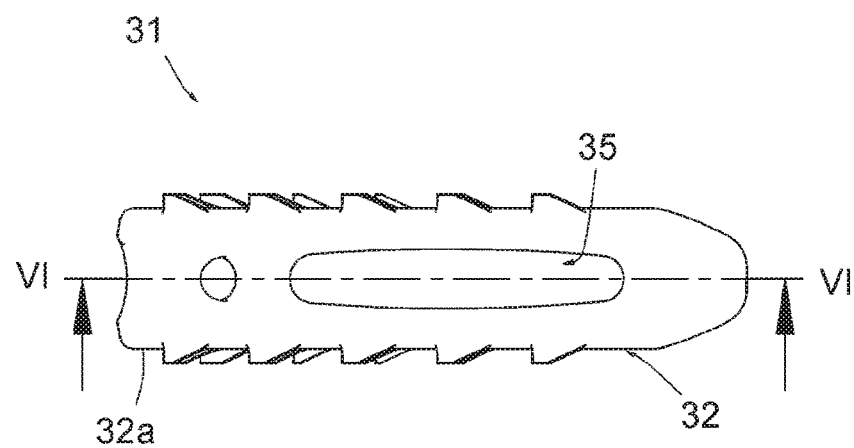
FIG. 5 is a side view of the implant according to a third embodiment, in this case made up of an intervertebral cage of the TLIF type.

The cage 21 shown in FIG. 4 has a structure similar to that of the cage 1, except that it is much wider and suitable for central placement in an intervertebral space.

This cage 21 comprises a cage body 22, a separating wedge 23 and bridges 24 for connecting said wedge to said cage body, the cage 21 being made using a method identical to that cited above used to produce the cage 1.

In this case, the wedge 23 is U-shaped, i.e., has two side branches engaged between the side portions of the upper and lower branches formed by the cage body 22, and has a central portion connected to the cage body 22 by the bridges 24.

Figure 8:
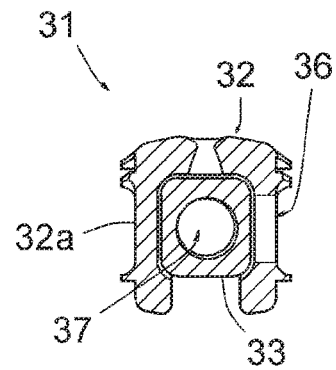
Figure 7:
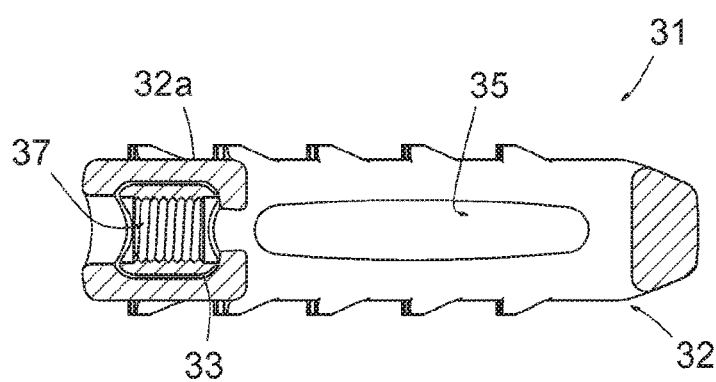
Figure 9:
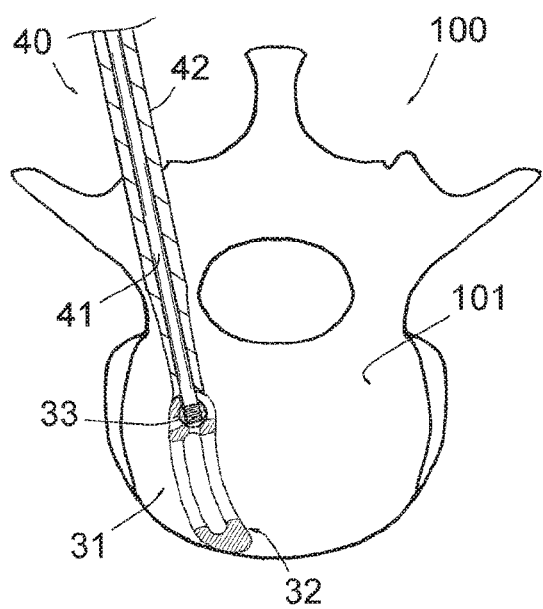
FIGS. 9 to 11 are top views of said implant and the instrument for placing it, during different successive steps of the placement of the implant in an intervertebral space.
Figure 10:
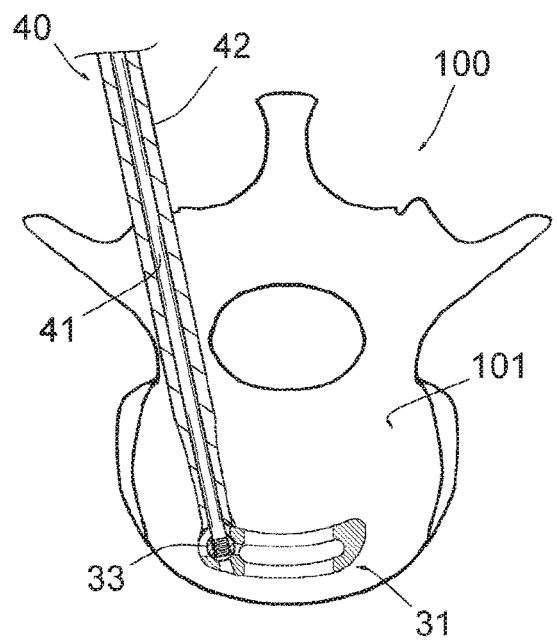
Figure 11:
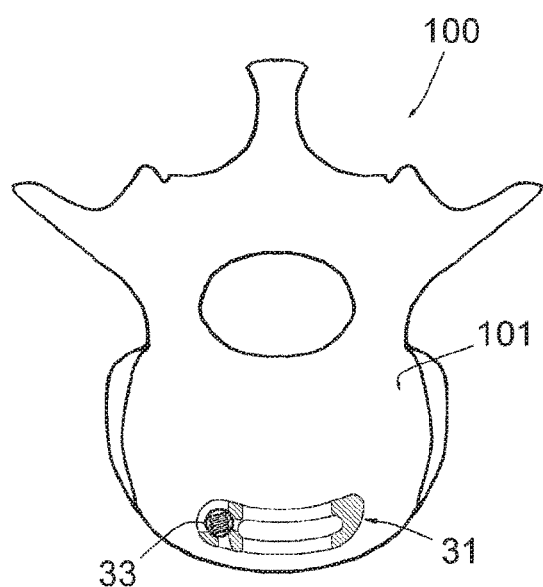

FIGS. 5 to 8 show an intervertebral cage 31 of the TLIF type, i.e., intended to be implanted using a transforaminal approach, as shown in FIGS. 9 to 11, using an instrument 40.

The cage 31 includes a cage body 32 and a cylinder 33 placed inside a bearing formed by a proximal portion 32a of the cage body 32, said proximal portion 32a partially enveloping said cylinder 33 so as to assemble said cylinder to the cage body 32. The cage 31 is made using the same method as that used to manufacture the cages 1 and 21, and the cylinder 33 is connected to the cage body 32 by one or several material bridges, not shown on the scale of the figures.

The cage body 32 has a curved general shape, suitable for placement on the anterior side of an intervertebral space 101, as shown in FIGS. 9 to 11, and forms a cavity 35 for receiving grafts or bone chips.

Figure 6:
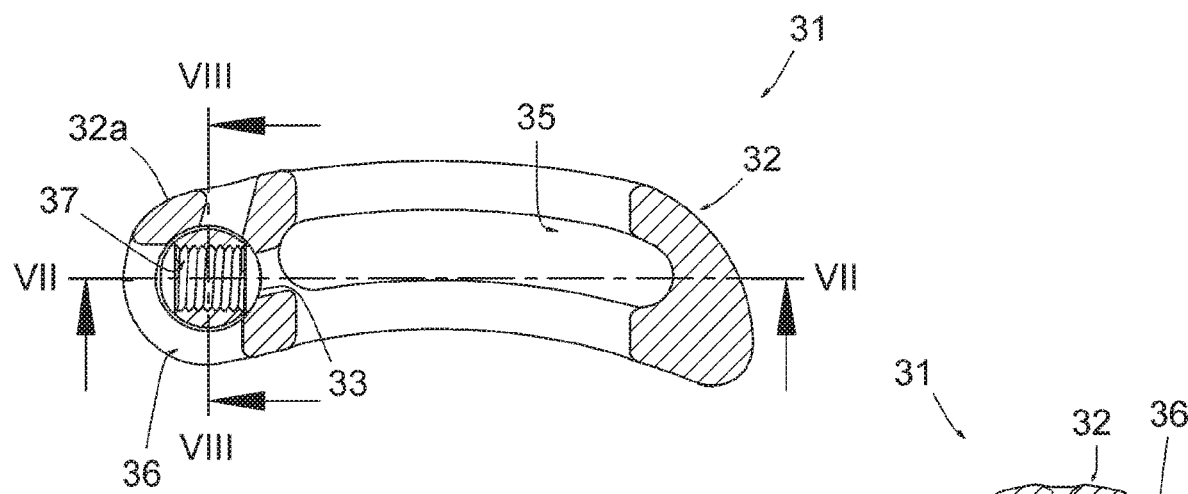
FIGS. 6 to 8 are cross-sections of this implant along lines VI-VI of FIG. 5 and VII-VII and VIII-VIII of FIG. 6, respectively.

FIGS. 6 and 8 show that the cage body 32 forms, at the portion 32a, a curved aperture 36, the curve of which is centered on the axis of said bearing, this aperture extending over about 90°, from an end located slightly withdrawn with respect to the longitudinal axis of the cage body 32 to its other end, located on the concave lateral side of the body 32.

The cylinder 33 is engaged fittingly in said bearing, but after breaking of the bridge(s) connecting it to the cage body 32, is able to pivot in this bearing around an axis perpendicular to the upper and lower surfaces of the cage body 32. Said cylinder 33 is pierced with a hole 37 inwardly forming a thread, which passes all the way through it, in which the threaded tip of a rod 41 included by the instrument 40 is capable of being screwed and unscrewed.

FIGS. 9 to 11 show that the instrument 40, aside from this rod 41, includes a body 42 able to bear against said proximal portion 32a. Said body 42 is passed through by the rod 41, which is movable axially and rotatably inside it.

The aforementioned bridges are broken in the plant, during manufacturing of the cage 31.

As will be understood in reference to FIGS. 6 to 9, the rod 41 is screwed through the hole 37 until it bears against the cage body 32, with the latter placed in an angular position such that the hole 37 is oriented parallel to the longitudinal axis of this cage body 32 (this longitudinal axis being that along which the cross-section is done along line VII-VII), the cage 31 thus being aligned with the instrument 40. This instrument 40 can therefore be used to insert the cage 31 into an intervertebral space 101 located between two vertebrae 100, until the cage 31 bears against the anterior ligaments (not shown) connecting these vertebrae 100, as shown in FIG. 9. Once the cage 31 has been inserted, the rod 41 is unscrewed so as to allow said cage to pivot relative to the longitudinal axis of the instrument 40, until it is adequate for positioning of the cage 31 in the intervertebral space 101, as shown in FIG. 10.

The rod 41 can then be unscrewed so as to be removed from the hole 37, allowing the instrument 40 to be removed, as shown in FIG. 11, this unscrewing providing an easy separation of the instrument 40 and the cage 31.

FIGS. 12 to 14 show a pedicle screw 51 in particular usable to fasten vertebral osteosynthesis equipment to at least two vertebrae needing to be immobilized relative to one another, using a well-known technique, in particular by the aforementioned patent application publication no. WO 98/55038.

Said pedicle screw 51 includes a body 52, a proximal pin 53 intended to be articulated relative to said body 52 and a frangible bridge 54 producing a connection of said proximal pin 53 to said body 52. The assembly is made using the same 3D printing method as that used to manufacture the aforementioned cages.

The body 52 forms a distal thread 55 for anchoring to the pedicle of a vertebra and a head 56 inwardly defining a spherical cavity in which a spherical head 57 of the pin 53 is contained. The wall forming said head 56 is closed on said head 57, such that the pin 53 remains assembled to the body 52 when the bridge 54 is broken.

The pin 53, aside from said head 57, has a threaded pin body 58, intended to receive a component for connecting to a vertebral bar and a nut for gripping this connecting component between it and the head 56, using a technique that is also well known.

FIGS. 15 and 16 show a laminar hook 61 very similar to the screw 51, therefore including a body 62, a threaded proximal pin 63 and a frangible bridge 54 for releasably connecting said pin to said body, the assembly also being manufactured using the same method as that cited above. The hook body 62 forms a head 66 defining a spherical cavity for receiving a corresponding spherical head 67, identical to what was described previously regarding the screw 51.

It emerges from the preceding that the invention provides a method for manufacturing an implant, in particular vertebral or intervertebral, having the decisive advantages of making it possible to produce a relatively simple and fast implant, with no subsequent assembly operations.

The invention has been described above in reference to embodiments provided solely as examples. It of course extends to all other embodiments covered by the appended claims.

The invention claimed is:

1. A method for manufacturing an implant, the implant comprising at least two components, at least a first component of which being intended to be movable relative to at least a second component, the method comprising the following steps:

designing the implant such that said second component at least partially envelops said first component; and such that at least one connecting bridge connects the first component to said second component, each bridge having a section such that it is frangible;

making the implant using a so-called "3D printing" method, consisting of:

depositing on a platen, a layer of powdered fusible material, causing the particles of this layer of powder to fuse in locations corresponding to the shape which, at this layer, said first component and/or said second component and/or said at least one bridge have, depending on whether said first component, said second component and/or said bridge are present at the section the implant to be formed has at said layer;

repeating these operations until the implant is fully constructed, and eliminating the powder particles that are not fused.

2. An implant obtained by the method according to claim 1, wherein the implant is an intervertebral cage having an anterior part, the height of which is able to be increased after implantation; said second component is made up of a cage body forming two branches which is deformable in this way such that anterior end portions of these branches are movable relative to one another between a close together position and a separated position; said first component is then made up of a separating wedge engaged between said branches connected to the cage body by said at least one bridge.

3. The implant obtained by the method according to claim 1, wherein the implant is an intervertebral cage wherein said first component is made up of a component of revolution and said second component is made up of a cage body forming a bearing for receiving and retaining this component of revolution; the component of revolution includes a means for connecting to an instrument for inserting/positioning the implant.

4. The implant according to claim 3, wherein said component of revolution is a cylinder.

5. The implant obtained by the process according to claim 1, wherein the implant is a polyaxial pedicle screw or a polyaxial laminar hook (61); said first component is formed by a connecting head or a threaded pin, and said second component is intended to be engaged with a vertebra to be treated.

6. The implant according to claim 5, wherein one from among said first component and said second component has an at least partially spherical portion and the other from among the first component and the second component has a corresponding at least partially spherical cavity intended to receive said at least partially spherical portion, said bridge being arranged between said at least partially spherical portion and the wall defining said at least partially spherical cavity.

* * * * *